United States Patent

Goethel

[11] Patent Number: 5,851,184
[45] Date of Patent: Dec. 22, 1998

[54] ELECTROCARDIOGRAPH CONTROL OF FLUID INJECTION

[75] Inventor: James H. Goethel, Cincinnati, Ohio

[73] Assignee: Liebel-Florsheim Company, Cincinnatti, Ohio

[21] Appl. No.: 754,893

[22] Filed: Nov. 22, 1996

[51] Int. Cl.[6] ................................................. A61B 6/00
[52] U.S. Cl. ............................................ 600/431; 604/31
[58] Field of Search ................................. 600/431, 432, 600/458, 407; 604/27, 28, 30, 31

[56] References Cited

U.S. PATENT DOCUMENTS

| | | | |
|---|---|---|---|
| 3,505,987 | 4/1970 | Heilman | 128/1 |
| 3,701,345 | 10/1972 | Heilman et al. | 128/2 R |
| 4,006,736 | 2/1977 | Kranys et al. | 128/2 A |
| 4,294,259 | 10/1981 | Picunko et al. | 600/431 |
| 4,585,008 | 4/1986 | Jarkewicz | 600/431 |
| 4,716,904 | 1/1988 | Meno | 600/431 |
| 4,729,379 | 3/1988 | Ohe | 600/431 |
| 4,854,324 | 8/1989 | Hirschman et al. | 128/655 |
| 4,903,705 | 2/1990 | Imamura et al. | 600/431 |
| 4,909,257 | 3/1990 | Engelstad et al. | 600/431 |
| 5,103,823 | 4/1992 | Acharya et al. | 600/431 |
| 5,417,213 | 5/1995 | Prince | 128/653.3 |

OTHER PUBLICATIONS

Medrad, Inc., *Medrad MCT Plus Front Load Injection System*, Medrad, Inc. Sales Brochure, No Date.
Liebel–Flarsheim, *Angoimat 6000 Digital Injection System*, Liebel–Flarsheim Sales Brochure, 1987.
Siemens Aktiengesellschaft, *Simtrac C*, Siemens Aktiengesellschaft Sales Brochure, No Date.
Liebel–Flarsheim, *Angiomat CT–Digital Injection System for Enhanced CT Scans*, Liebel–Flarsheim Sales Brochure, 1988.
E–Z–EM, *Simple the Best Value in Low–Pressure CT Injection Systems, Percūpump 1A*, Therapex, Division of E–Z–EM Canada, Inc., Sales Brochure, 1990.

Primary Examiner—Brian Casler
Attorney, Agent, or Firm—Wood, Herron & Evans L.L.P.

[57] ABSTRACT

An electrocardiograph controlled injection continues until a programmed amount of contrast media has been injected, rather than until a predetermined number of heart cycles has been experienced. As a result, if injections are terminated early due to a PVC in the patient's heart rhythm, the injector will continue to attempt injections for an indefinite number of subsequent heart cycles, until the programmed volume of contrast media has been injected, rather than terminating operation after a set number of injections.

4 Claims, 2 Drawing Sheets

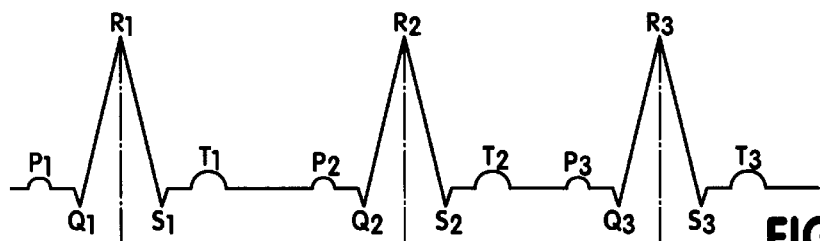
FIG. 1A
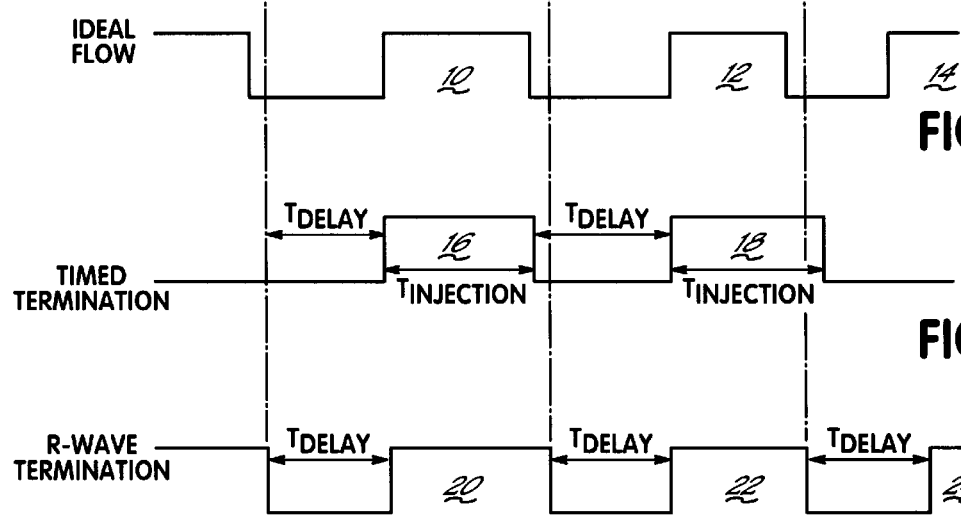
FIG. 1B
FIG. 1C
FIG. 1D
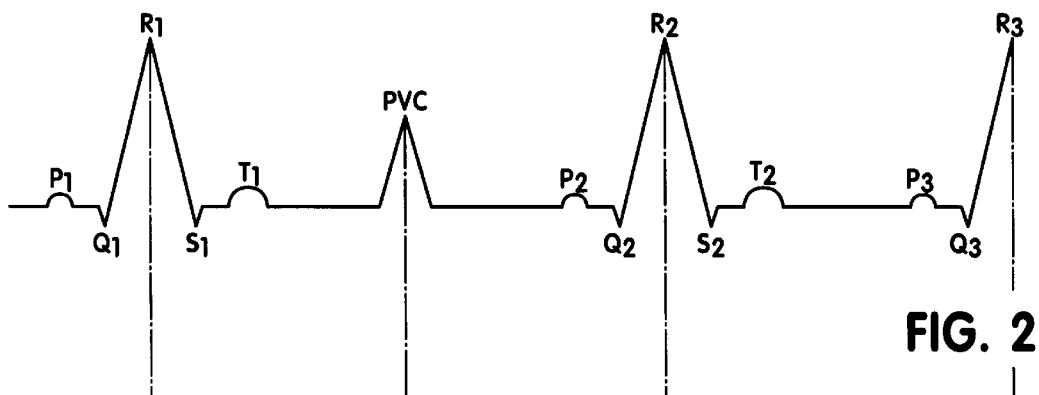
FIG. 2A
FIG. 2B

ELECTROCARDIOGRAPH CONTROL OF FLUID INJECTION

FIELD OF THE INVENTION

The present invention relates to methods for injecting contrast media into animals for medical imaging.

BACKGROUND OF THE INVENTION

In medical imaging, a contrast media is often injected into a patient to improve CT, Angiographic, Magnetic Resonance or Ultrasound imaging, using a powered, automatic injector. As one example, contrast media is often injected into the patient's blood stream to facilitate imaging of soft tissues such as arteries.

This method is also used to image soft tissue in the heart, to assess the strength of the heart muscle and/or view its movements. In such environments, contrast media is injected into the heart while the heart is beating, so that the structure of the heart and its movements become visible on an imaging screen.

As an example of such a procedure, to image the left ventricle of the heart (which pumps blood through the aorta to the entirety of the body) a catheter is inserted into a patient's artery, fed upstream (opposite to the direction of blood flow) into the aorta, and into the left ventricle through the aortic valve of the heart. Once the catheter has been appropriately inserted, contrast media can then be delivered directly into the left ventricle of the heart through the catheter, enhancing imaging.

Typically, it is desirable to synchronize injection of fluid with the beats of the subject's heart, so as to inject fluid into the left ventricle while the left ventricle is filling with blood from the left atrium, as opposed when the left ventricle is pumping blood into the aorta. Doing so reduces the strain on the patient's heart and also increases the duration of time that contrast media remains in the left ventricle, improving imaging.

To accomplish such synchronization, it has been known to include an ECG controlled mode in a contrast media injector. When in ECG controlled mode, the injector will respond to the patient's electrocardiograph (ECG) signal, to initiate or terminate injection.

FIG. 1A illustrates a typical ECG signal for a human patient. Each heartbeat is associated with a sequence of waveforms known as the P, Q, R, S and T waves. Three P-Q-R-S-T complexes are shown in FIG. 1A. The left ventricle fills with blood from the left atrium generally during the period between the T wave of a preceding heartbeat and the R wave of the subsequent heartbeat. Thus, the heart fills with blood in the time periods between $T_1$ and $R_2$ between $T_2$ and $R_3$, and beginning after $T_3$.

FIG. 1B illustrates an ideal injection flow pattern for the ECG waveform illustrated in FIG. 1A. As seen in FIG. 1B, injection of contrast media into the left ventricle should be made in the time periods 10, 12 and 14 which correspond to the above-noted periods when the heart is filling with blood.

In one known method for controlling an injector to approximately produce the ideal injection pattern of FIG. 1B, the injector initiates injection a time $T_{DELAY}$ after detecting an R-wave in the ECG signal. Once initiated, the injection continues for a time $T_{INJECTION}$. After the injection is complete, the injector again awaits an R-wave to restart another injection.

A known enhancement to this method terminates injection when the injector detects an R-wave rather than at the end of the predetermined time $T_{INJECTION}$. This enhancement ensures that injection will be terminated before the left ventricle begins pumping blood into the aorta while producing the maximum possible injection time.

In either method, typically the injector is programmed to inject contrast media for a fixed number, e.g., 10 cycles of the patient's heart. After these 10 cycles, the injector ceases injecting fluid.

SUMMARY OF THE INVENTION

A difficulty with the first methodology described above, is the need to adjust the times $T_{DELAY}$ and $T_{INJECTION}$ so that the total of these times is less than the time between heart beats. As seen in FIG. 1C, when these times are appropriately set, the injection period, such as period 16 will be correctly synchronized to the beats of the patient's heart. However, if these time periods are set inaccurately, for example if the time between heart beats is less than the time $T_{DELAY}+T_{INJECTION}$, entire heart cycles will be missed and contrast media will be injected into the left ventricle at undesirable times. For example, as seen in FIG. 1C, although an appropriate injection flow is produced during time period 16, an inappropriate injection flow is produced during time period 18 due to a sudden increase in heart rate between the second and third heart beats (indicated by a shorter time between waves $R_2$ and $R_3$ as compared to the time between waves $R_1$ and $R_2$. Due to this sudden heart rate increase, the time $T_{DELAY}+T_{INJECTION}$ is longer than the time between waves $R_2$ and $R_3$, with the result that injection flow period 18 continues after wave $R_3$, i.e., overlaps that period of time when the left ventricle is pumping blood into the aorta. Furthermore, because injection flow 18 ends after R wave $R_3$, no injection flow commences in the time period after T wave $T_3$, causing the injector to fail to introduce media during this cycle. If the heart continues at this increased pulse rate, the injector will continue to inject contrast media at undesirable times, and to inject contrast media during alternate heart beats, dramatically reducing the ability of an operator to obtain useful imaging of the heart.

As noted above, it is known to configure the injector to terminate injection when an R-wave is detected, so as to prevent injection of contrast media into the heart while the heart is pumping blood into the aorta. Unfortunately, this approach creates a second difficulty, illustrated in FIGS. 2A and 2B.

Heart rhythms often include a premature ventricular contraction (PVC). The waveform PVC (FIG. 2A) associated with a premature ventricular contraction resembles an R wave, and is distinguishable primarily by the fact that it appears outside of a normal P-Q-R-S-T complex.

Unfortunately, an injector is often unable to distinguish a PVC from an R wave. Accordingly, if R wave termination is used for an injection (to avoid the difficulties with timed termination noted above), injection will typically be prematurely terminated by a PVC. As seen in FIG. 2B, in such a circumstance, although an appropriate injection will be made in time periods such as 28 where there is no PVC, when there is a PVC the injection period will be cut short such as shown in period 26. Thereafter, another short injection such as 27 may be initiated, but it, too, will be cut short by the next R-wave. The amount of contrast media injected into the heart during these short periods 26 and 27 is insufficient for adequate imaging.

A second difficulty arises from the fact that a typical injector only operates for a preprogrammed number, e.g. 10, heart cycles, and then ceases injection. If the patient has a fairly regular PVC, the heart will receive a full injection of contrast media during only a few of these 10 heart cycles, and once the 10 cycles are completed, the operator will be required to reset the injector for an additional set of heart cycles to obtain further images. For a patient with a regular PVC, the resulting repeated reprogramming of the injector can be frustrating and time consuming.

In accordance with the invention, these difficulties are overcome by a novel methodology for performing an ECG controlled injection. Specifically, in accordance with the invention, an ECG controlled injection is programmed to continue until a programmed amount of contrast media has been injected, rather than until a predetermined number of heart cycles has been experienced. As a result, the above-noted difficulties with R-wave termination are substantially ameliorated. If injections are terminated early due to a PVC in the patient's heart rhythm, the injector will continue to attempt injections for an indefinite number of subsequent cycles, until the programmed volume of contrast media has been injected, rather than terminating operation after a set number of injections.

In the disclosed preferred embodiment of this methodology, the injector terminates injection after a predetermined volume, regardless of whether the injector is configured to perform R-wave termination or timed termination. However, the benefits of the invention are most apparent when R-wave termination is enabled, for the reasons noted above.

The above and other features, aspects, objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 1A is a schematic drawing of a typical electrocardiograph waveform;

FIG. 1B is a timing diagram of an ideal contrast media injection flow in response to the waveform of FIG. 1A;

FIG. 1C is a timing diagram of a contrast media injection flow produced in response to the waveform of FIG. 1A using timed injection termination;

FIG. 1D is a timing diagram showing R-wave termination.

FIG. 2A is a schematic drawing of an electrocardiograph waveform having a PVC;

FIG. 2B is a timing diagram of a contrast media injection flow produced in response to the waveform of FIG. 2A using with R-wave termination of injections.

DETAILED DESCRIPTION OF SPECIFIC EMBODIMENTS

Figure 3:
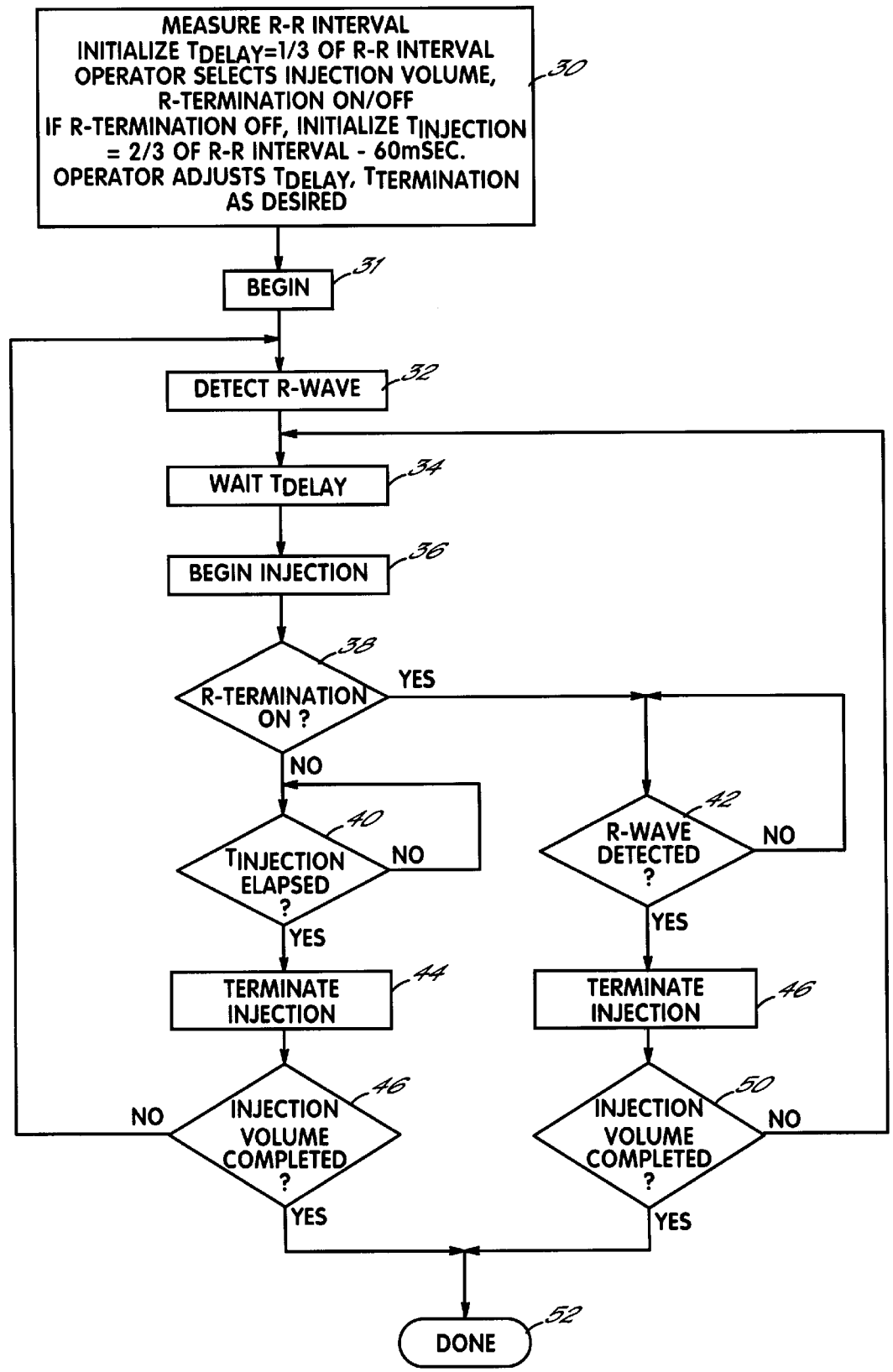
FIG. 3 is a flow chart for a method for electrocardiograph control of contrast media injection in accordance with principles of the present invention.

Injection apparatus for carrying out principles of the present invention are disclosed in U.S. Pat. Nos. 4,650,465, 4,812,724, 5,279,569, and co-pending U.S. patent application Ser. No. 08/494,795 in the name of Kenneth Niehoff, and U.S. patent application Ser. No. 08/753,288, entitled "MEDICAL FLUID INJECTOR", filed concurrently herewith, all of which are assigned to the same assignee as this application, and are hereby incorporated by reference in their entirety.

The present invention may be carried out by appropriate programming of any of the injector apparatus described in the above-referenced U.S. patents and applications. Referring now to FIG. 3, details of such programming can be more fully understood.

As an initial step 30, the injector measures the R—R interval of the patient's ECG waveform. Next, the delay time $T_{DELAY}$ is initialized to a value which is ⅓ of the measured R—R interval. Then, the operator uses the injector user interface to define the total injection volume desired, and to indicate whether R-wave termination should be used. If R-wave termination is not selected by the operator, the injection time $T_{INJECTION}$ is initialized to a value which is 60 msec less than ⅔ of the measured R—R interval. Once this initialization is completed, the operator can adjust the delay time $T_{DELAY}$ and (if R-wave termination is not used) the injection time $T_{INJECTION}$ as desired by the operator.

After setting these parameters, the operator appropriately positions the catheter in the patient and starts the injector (step 31).

During each heart cycle of the injection, the injector monitors the ECG from the patient (or a synchronization signal provided by an ECG monitor) to detect 32 an R-wave. When an R-wave has been detected, the injector waits 34 for the preprogrammed delay time $T_{DELAY}$, and then begins injection of contrast media (step 36).

At this point, the injector must perform alternate operations based on whether the operator has enabled R-wave termination, and so performs a branch (step 38) based on whether R-wave termination is enabled.

If R-wave termination is not enabled, the injector proceeds from step 38 to step 40, and remains in step 40 until the injection time $T_{INJECTION}$ has elapsed. Thereafter, the injector terminates the injection (step 44), and subsequently determines (step 48) whether the total volume of fluid injected has equaled the injection volume specified by the operator in step 30. If not, the injector returns to step 32 to await detection of a subsequent R-wave.

If R-wave termination is enabled, the injector proceeds from step 38 to step 42, and remains in step 42 until a subsequent R-wave is detected. Upon detection of a subsequent R-wave, the injector terminates the injection (step 46), and subsequently determines (step 50) whether the total volume of fluid injection has equaled the injection volume specified by the operator in step 30. If not, the injector returns to step 34 to wait the delay time $T_{DELAY}$, and then begin the next injection.

If, at either step 48 or step 50, the total injection volume equals the injection volume specified by the operator in step 30, the injector proceeds to step 52, and is completed with the ECG-controlled injection.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

I claim:

1. A method for performing injection of contrast media into a patient in synchrony with said patient's heart rhythm, comprising selecting a predetermined total volume of contrast media to be injected into said patient, detecting an electrocardiograph of said patient's heart rhythm;

detecting an R-wave in said electrocardiograph;

initiating injection of contrast media into said patient a predetermined delay time after detecting said R-wave;

terminating injection of contrast media into said patient upon detection of an R-wave; and repeating said detecting, initiating and terminating steps until said predetermined total volume of contrast media has been injected into said patient regardless of a number of repetitions of said detecting, initiating and terminating steps.

2. The method of claim 1 wherein said step of terminating injection of contrast media comprises terminating injection of contrast media a predetermined injection time after initiating injection.

3. Apparatus for performing injection of contrast media into a patient in synchrony with said patient's heart rhythm, comprising a sensor detecting an electrocardiograph of said patient's heart rhythm;

a control system controlling an injection operation, by selecting a predetermined total volume of contrast media to be injected into said patient, detecting an R-wave in said electrocardiograph, initiating injection of contrast media into said patient a predetermined delay time after detecting said R-wave, terminating injection of contrast media into said patient upon detection of an R-wave; and repeating the detecting, initiating and terminating until said predetermined total volume of contrast media has been injected into said patient regardless of a number of repetitions of the detecting, initiating and terminating.

4. The apparatus of claim 3 wherein said control system terminates injection of contrast media a predetermined injection time after initiating injection.

* * * * *